(12) United States Patent
Beach et al.

(10) Patent No.: US 9,063,049 B2
(45) Date of Patent: Jun. 23, 2015

(54) APPARATUS AND METHOD FOR QUANTIFYING METAL SURFACE TREATMENT

(71) Applicant: Hydro Honing Laboratories, Inc., East Hartford, CT (US)

(72) Inventors: Thomas A. Beach, West Hartford, CT (US); Walter A. Beach, Suffield, CT (US)

(73) Assignee: Hydro Honing Laboratories, Inc., East Hartford, CT (US)

( * ) Notice: Subject to any disclaimer, the term of this patent is extended or adjusted under 35 U.S.C. 154(b) by 406 days.

(21) Appl. No.: 13/670,648

(22) Filed: Nov. 7, 2012

(65) Prior Publication Data

US 2013/0133398 A1     May 30, 2013

Related U.S. Application Data

(60) Provisional application No. 61/629,747, filed on Nov. 25, 2011.

(51) Int. Cl.
| | |
|---|---|
| *G01N 3/62* | (2006.01) |
| *G01M 5/00* | (2006.01) |
| *G01N 3/30* | (2006.01) |

(52) U.S. Cl.
CPC .. *G01N 3/62* (2013.01); *G01N 3/30* (2013.01); *G01N 2203/0298* (2013.01); *G01N 2203/0664* (2013.01); *G01M 5/00* (2013.01); *G01N 2203/0246* (2013.01)

(58) Field of Classification Search
CPC .............. G01N 2203/0244; G01N 2203/0246; G01N 2203/0298; G01N 2203/0664; G01N 3/30; G01N 3/62; G01M 5/00

USPC ........................................................ 73/11.02
See application file for complete search history.

(56) References Cited

U.S. PATENT DOCUMENTS

| | | | | |
|---|---|---|---|---|
| 2,607,213 | A | * | 8/1952 | Barton ........................ 73/11.02 |
| 3,638,464 | A | | 2/1972 | Winter et al. |
| 5,731,509 | A | | 3/1998 | Thompson |
| 6,502,449 | B1 | * | 1/2003 | Baiker ........................ 73/11.02 |
| 6,568,239 | B1 | | 5/2003 | Champaigne |
| 7,735,350 | B2 | * | 6/2010 | Bailey et al. ................. 73/11.02 |
| 2010/0077831 | A1 | * | 4/2010 | Bailey et al. ................. 73/11.02 |
| 2012/0017661 | A1 | * | 1/2012 | Yamada et al. .................. 72/53 |

* cited by examiner

*Primary Examiner* — Peter Macchiarolo
*Assistant Examiner* — Nathaniel Kolb
(74) *Attorney, Agent, or Firm* — MKG, LLC

(57) ABSTRACT

A method for measuring a metal surface treatment of a metal component includes creating a solid model of the metal component, identifying surface locations on the metal component at which a set of structural properties is specified by design, and identifying a simulated location on the solid model corresponding to the identified surface location on the metal component. The method includes preparing a simulation fixture plan for fabricating a simulation fixture having an element for supporting a test strip holder thereon at the identified simulated location, and then fabricating the simulation fixture. A test strip holder is positioned at the identified simulated location on the simulation fixture, and a test strip is positioned in the test strip holder. The simulation fixture is subjected to the metal surface treatment wherein the simulation fixture has the test strip holder positioned thereon and the test strip holder has the test strip positioned thereon.

20 Claims, 12 Drawing Sheets

APPARATUS AND METHOD FOR QUANTIFYING METAL SURFACE TREATMENT

CROSS-REFERENCE TO RELATED APPLICATION

This application claims the benefit of U.S. Provisional Patent Application Ser. No. 61/629,747; filed on Nov. 25, 2011, which provisional patent application is incorporated herein by reference in its entirety.

FIELD OF INVENTION

The present invention is generally related to an apparatus and a method for evaluating the surface of a metal component after the metal component has been subjected to a surface treatment process. In particular, the present invention relates to an apparatus and a method for properly locating a device for measuring the intensity of a metal surface treatment process wherein the metal component exhibits a complex geometry.

BACKGROUND OF THE INVENTION

In brief, shot peening is a cold metal-working process that produces a compressive residual stress layer in a subject metal component and concurrently modifies the mechanical properties of that metal component. Shot peening comprises impacting a surface of the subject metal component with round metallic, glass, or ceramic particles, commonly referred to as "shot." The force at which the shot strikes the surface of the subject metal component, and correspondingly produces a compressive residual stress layer in the subject metal component, is application-specific.

It is well known in the art that the process of shot peening increases fatigue strength in the subject metal component by relieving tensile stresses that contribute to stress-corrosion cracking. In conventional shot peening processes, spheroid particles of cast steel, cast iron, glass, etc., are blown or mechanically impelled in a high velocity stream against the surface to be treated. The individual shot particles produce shallow, rounded overlapping dimples in the surface, stretching it radially from each point of impact and causing cold working and plastic flow. The resultant compressive stress tends to counteract tensile stresses imparted to the surface by preceding rolling, bending, abrading, and similar processes that occur during the manufacturing of the subject metal component.

Two critical shot peening factors are "peening intensity" and "coverage." Peening intensity is a function of the weight, size, hardness and velocity of the peening particles, angle of impingement, and various other factors. Accordingly, peening intensity is a function of the kinetic energy of the shot impacted upon the surface of the component. In summary, it is a function of shot velocity and size. Shot is accelerated by using air pressure to force it through a peening nozzle or accelerated centrifugally via a wheel and directed at the component's surface. Coverage rate or the rate of approach to saturation depends on dimple size, the rate of dimple accumulation and statistics.

The use of a test strip or coupon, such as for example an Almen strip, is well known for measuring shot peening intensity and has been referred to as a key element in shot peening process control. Developed and patented by John O. Almen, Almen strips comprise thin metal strips that deflect when subjected to shot peening. A test strip or coupon, or an Almen strip, is mounted in a special holder wherein a critical section of the strip is exposed. Thus, the Almen strip mounted in the special holder is exposed to the shot stream under substantially the same conditions as the subject metal component undergoing peening.

Almen strips deflect in response to the surface compression produced by shot impacts. One impact causes some deflection of the strip toward the side struck. As the impacts accumulate, the deflection increases. Deflection is also greater if the impacts are more energetic, for example comprising higher shot velocity and diameter. The Almen strip is a convenient way of assessing the overall peening process.

An Almen strip is clamped in a special fixture and peened under a given set of conditions, such as, gun air pressure, shot size and shot mass flow rate. The deflections of many strips peened under these conditions and for varying amounts of time are then plotted on what is known as a saturation curve. Saturation is said to occur when doubling the peening time has a 10% effect on deflection. For practical purposes, at saturation the strip is fully covered with impact dimples so its deflection is proportional only to the peening intensity. Generally, peening of the subject component parts may begin at this saturation intensity.

Almen strips are classified into three (3) types: "A", "N" and "C". They differ in thickness and define the same width and length. Typical Almen strips are made from SAE 1070 cold rolled spring steel and have surface dimensions of 0.75 inch×3.00 inches. Almen strips are commercially available in three thicknesses: 0.031 inch ("N"-strips); 0.051 inch ("A"-strips); and 0.093 inch ("C"-strips).

SUMMARY OF THE INVENTION

According to aspects illustrated herein, there is provided a method for measuring a metal surface treatment of a metal component that includes creating a solid model of the metal component, identifying at least one surface location on the metal component at which a set of structural properties is specified by design, and identifying a simulated location on the solid model corresponding to the identified surface location on the metal component. The method further includes preparing a simulation fixture plan for fabricating a simulation fixture that has an element for supporting a test strip holder thereon at the identified simulated location, and then fabricating the simulation fixture. At least one test strip holder is positioned at the identified simulated location on the simulation fixture, and a test strip is positioned in the test strip holder. The simulation fixture is subjected to the metal surface treatment wherein the simulation fixture has the test strip holder positioned thereon and the test strip holder has the test strip positioned thereon.

According to other aspects illustrated herein, there is provided a method for establishing the operating parameters of a shot peening process of a metal component including creating a solid model of the metal component, identifying surface locations on the metal component at which a set of structural properties is measured, and identifying a simulated location on the solid model corresponding to each identified surface location on the metal component. The method further includes preparing a simulation fixture plan for fabricating a simulation fixture that has an element for supporting a test strip holder thereon at each identified simulated location, and then fabricating the simulation fixture. A test strip holder is positioned at each identified simulated location on the simulation fixture, and a test strip is positioned in each test strip holder. The simulation fixture is subjected to the shot peening process wherein the simulation fixture has the test strip holders positioned thereon and the test strip holders have the test strip positioned thereon. At least one of the test strips is removed from a respective test strip holder positioned on the simulation fixture, and the test strip is examined for arc height and uniform coverage. A set of results is obtained and analyzed, and the shot peening process is fine-tuned based upon the analysis of the set of results of the examination of the test strip. A replacement test strip is positioned in each of the respective test strip holders positioned on the simulation fixture from which the test strip was removed. The simulation fixture is subjected to the fine-tuned shot peening process wherein the simulation fixture has the test strip holders positioned thereon and the test strip holders have the test strip positioned thereon.

According to still other aspects illustrated herein, there is provided a method for shot peening a metal component including creating a solid model of the metal component, identifying at least one surface location on the metal component at which a set of structural properties is measured, and identifying a simulated location on the solid model corresponding to each identified surface location on the metal component. The method further includes preparing a simulation fixture plan for fabricating a simulation fixture that has an element for supporting a test strip holder thereon at each identified simulated location, and then fabricating the simulation fixture. A test strip holder is positioned at each identified simulated location on the simulation fixture, and a test strip is positioned in each test strip holder. The simulation fixture is subjected to the shot peening process wherein the simulation fixture has the test strip holders positioned thereon and the test strip holders have the test strip positioned thereon. At least one of the test strips from the respective test strip holder positioned on the simulation fixture, and the test strip is examined for at least one of shot peening intensity, coverage, and deflection. A set of results is obtained and analyzed and the shot peening process is fine-tuned based upon the analysis of the set of results of the examination of the test strip. A replacement test strip is positioned in each of the respective test strip holders positioned on the simulation fixture from which the test strip was removed. The simulation fixture is subjected to the fine-tuned shot peening process wherein the simulation fixture has the test strip holders positioned thereon and the test strip holders have the test strip positioned thereon. The method further includes repeating the steps of removing at least one of the test strips from the respective test strip holder positioned on the simulation fixture, examining the test strip, obtaining and analyzing a set of results, and fine-tuning the shot peening process until the set of results is within an acceptable range. Subsequently, the metal component is subjected to the fine-tuned shot peening process, and at least one of the identified surface locations on the metal component is examined and analyzed for the set of structural properties specified by design.

DESCRIPTION OF THE INVENTION

An apparatus and method for quantifying metal surface treatment in accordance with the present invention provides for evaluating a complex geometry of a metal component and a precise surface or plurality of surfaces to be subjected to a metal surface treatment process, such as, for example, shot peening. Engineers and designers of a numerous metal components generally require that a particular component function under precise operating parameters. Such operating parameters often require that the particular component exhibit inherent characteristics. Often, the particular component must be subjected to various metal surface treatment processes such as shot peening to incorporate those necessary characteristics.

The present invention comprises an apparatus and a method for properly locating a plurality of Almen strip mounting blocks at precise locations of a multifaceted metal component to ensure that any one of a plurality of selected surfaces have been subjected to the correct shot peening intensity. Accordingly, the metal component exhibits the metallurgical capabilities and structural properties specified for its application; such as, for example, tensile stress, compressive stress, sheer strength, grain alignment, hardness, plasticity, etc. Such metallurgical capabilities and structural properties are specified by a design engineer, for example, such that the subject part functions as intended in any one of a plurality of applications such as, for example, aerospace, automotive, marine, medical, power generation, armaments, industrial machinery, and the like.

Figure 1:
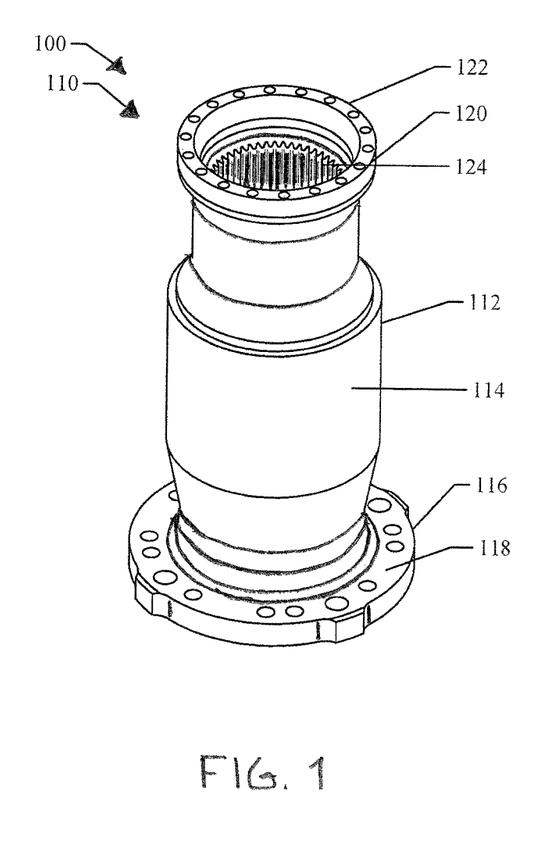
FIG. 1 is an isometric projection of a metal component having a complex geometry and defining a plurality of surfaces to be subjected to a metal surface treatment process in accordance with the present invention.

An exemplary metal component having a complex geometry and defining a plurality of surfaces to be subjected to a metal surface treatment process, such as for example shot peening, is shown in FIG. 1, and is referred to generally as component 100. A first step in an illustrated embodiment of a method of the present invention for quantifying the metal surface treatment of component 100 comprises creating a solid model 110 of the component 100. Preferably, the solid model 110 is a digital model generated using computer-aided design ("CAD") or computer-aided design and drafting ("CADD") software and related computer hardware, server, and peripheral systems to assist in the creation, examination and optimization of the solid model 110. A three-dimensional ("3-D") representation of the solid model 110 is generated as well as two-dimensional ("2-D") sketches of various elements of the solid model 110.

Figure 2A:
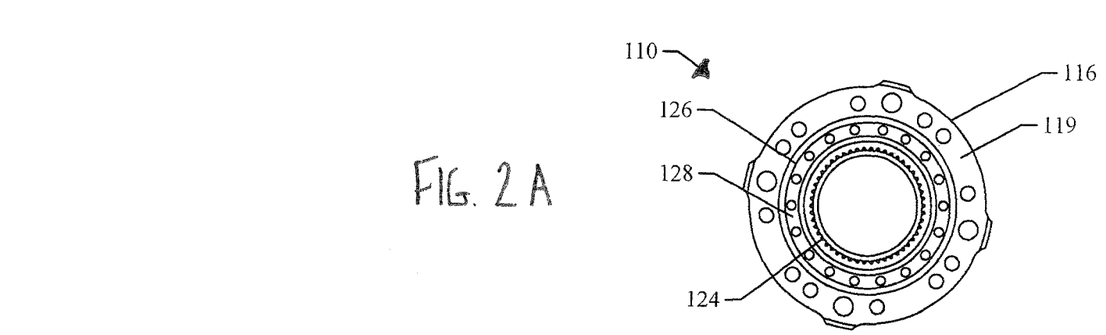
FIG. 2A is a top plan view of the metal component of FIG. 1.
Figure 2B:
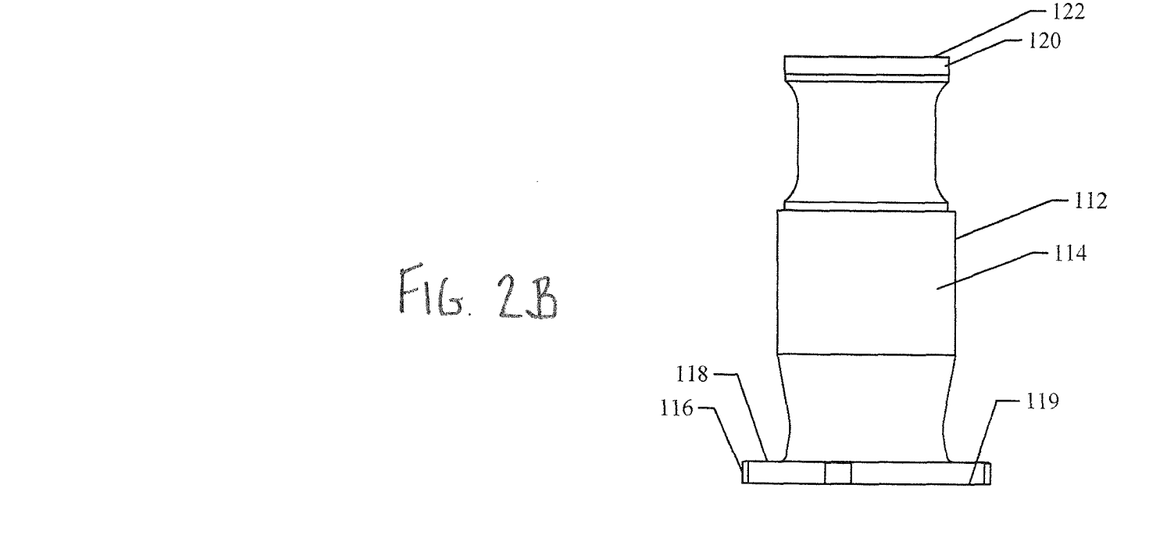
FIG. 2B is a side view of the metal component of FIG. 1.

As further shown in FIGS. 1, 2A and 2B, the solid model 110 of the component 100 includes a body 112 having an exterior surface 114, a base flange 116 having a top face 118 and a bottom face 119, and a top flange 120 having a top face 122. The body 112 of the solid model 110 is substantially cylindrical and the base flange 116 and top flange 120 are substantially circular. Component 100, and therefore the solid model 110, also includes an internal spline 124 for engaging an external spline of a rotating part such as a shaft (not shown). While the solid model 110 has been shown and described as having a substantially cylindrical body 112 and substantially circular base and top flanges 116 and 120 respectively, the present invention is not limited in this regard as the component 100 may define any geometry having at least one surface that will be subjected to a metal surface treatment process without departing from the broader aspects of the present invention.

Figure 3A:
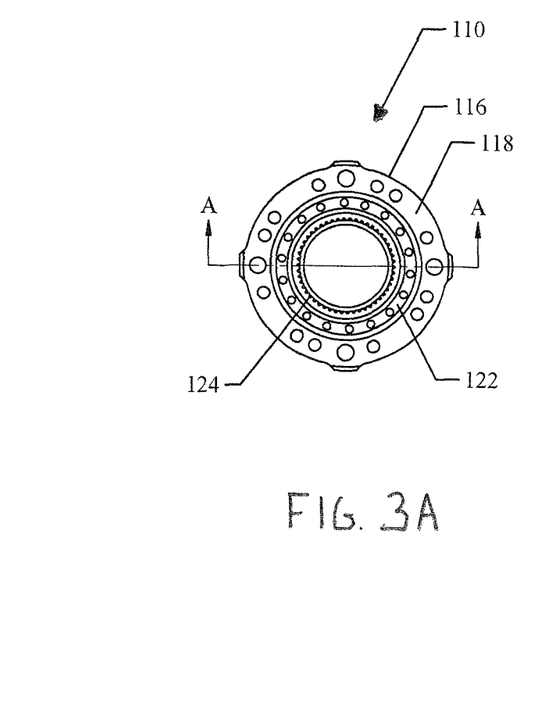
FIG. 3A is a top plan view of the metal component of FIG. 1.
Figure 3B:
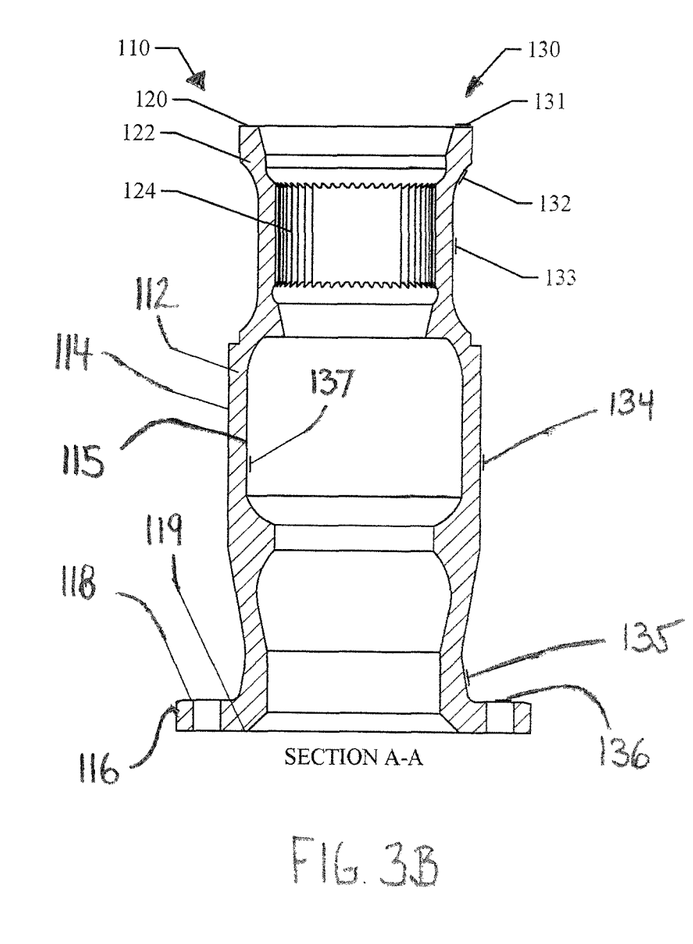
FIG. 3B is a cross-section of the metal component of FIG. 1 taken along line A-A of FIG. 3A.

A second step in the illustrated embodiment of the method for quantifying the metal surface treatment of component 100 comprises identifying or selecting locations on the component 100 at which a set of structural properties is specified by design for the component 100, and identifying or selecting corresponding locations 130 on the solid model 110 at which the intensity of the metal surface treatment process, in this embodiment the shot peening process, is quantified, measured, and/or verified. As depicted in FIG. 3B, the body 112 of solid model 110 also comprises an interior surface 115. The locations 130 identified or selected as suitable locations for quantifying the metal surface treatment of component 100 are shown on the solid model 110 (FIG. 3B) as: location 131 on the top face 122 of the top flange 120; locations 132, 133, 134 and 135 on the exterior surface 114 of the body 112; location 136 at the top face 118 of the base flange 120; and location 137 on the interior surface 115 of the body 112.

Figure 4:
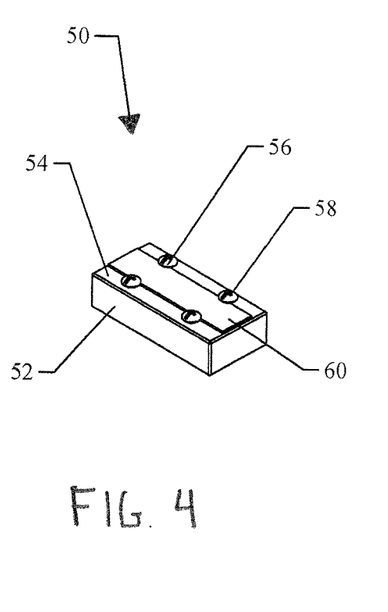
FIG. 4 is an isometric projection of an Almen strip mounting block.

A third step in the illustrated embodiment of the method for quantifying the metal surface treatment of component 100 comprises properly locating at least one Almen strip mounting block having a test strip, preferably an Almen strip, mounted thereon, and preferably a plurality of Almen strip mounting blocks wherein each said mounting block has an Almen strip mounted thereon. A test strip mounting block assembly is depicted in FIG. 4 and is generally designated by the reference number 50. The test strip mounting block assembly 50 includes an Almen strip or similar test strip holder or block 52 having a top face 54, and a fastener 56, such as for example machine screws 58, for mounting a test strip 60 onto the block 52. While machine screws are shown and described, the present invention is not limited in this regard as other types of fasteners suitable for retaining a test strip on a test strip holder, such as for example spring-retention clips, may be substituted without departing from the broader aspects of the present invention. The test strip mounting block assembly 50 is more fully described in U.S. patent application Ser. No. 13/365,896 filed on Feb. 3, 2012, which patent application is incorporated herein by reference in its entirety.

Figure 5:
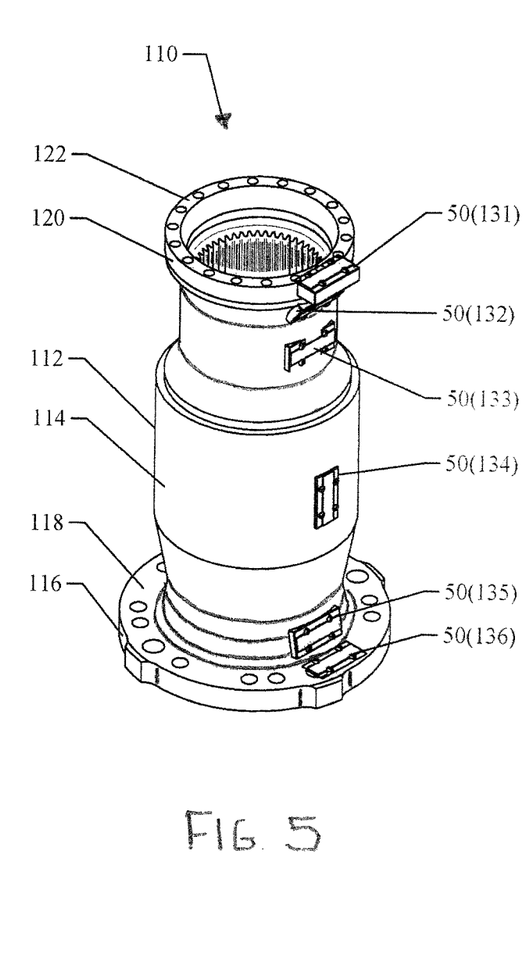
FIG. 5 is an isometric projection of the metal component of FIG. 1 having a plurality of the Almen strip mounting blocks of FIG. 4 mounted thereon.
Figure 6A:
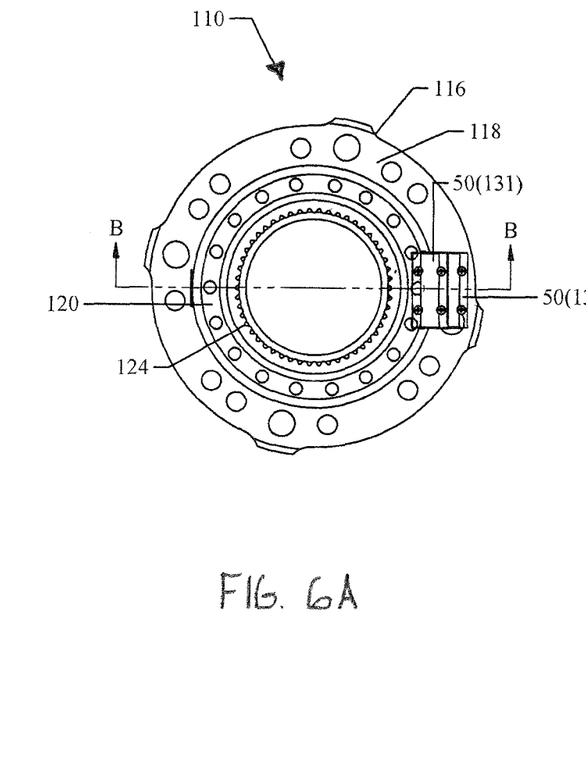
FIG. 6A is a top plan view of the metal component of FIG. 5.
Figure 6B:
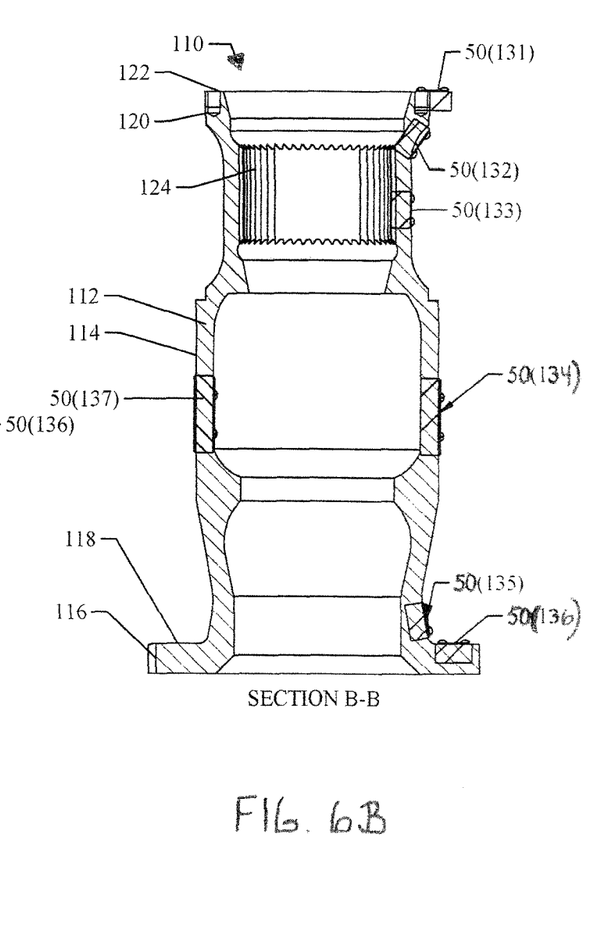
FIG. 6B is a cross-section of the metal component of FIG. 5 taken along line B-B of FIG. 6A.

Continuing with the third step in the illustrated embodiment of the method for quantifying the metal surface treatment of component 100 and as shown in FIGS. 5, 6A and 6B, the test strip mounting block assembly 50 is positioned at locations 131-137 (shown in the figures as "50 (location identification)"). Accordingly, an Almen test strip 60 is positioned at each location identified on the component 100, and correspondingly on the solid model 110, where the intensity of the metal surface treatment process, in this embodiment the shot peening process, is quantified, measured, and/or verified.

Figure 7A:
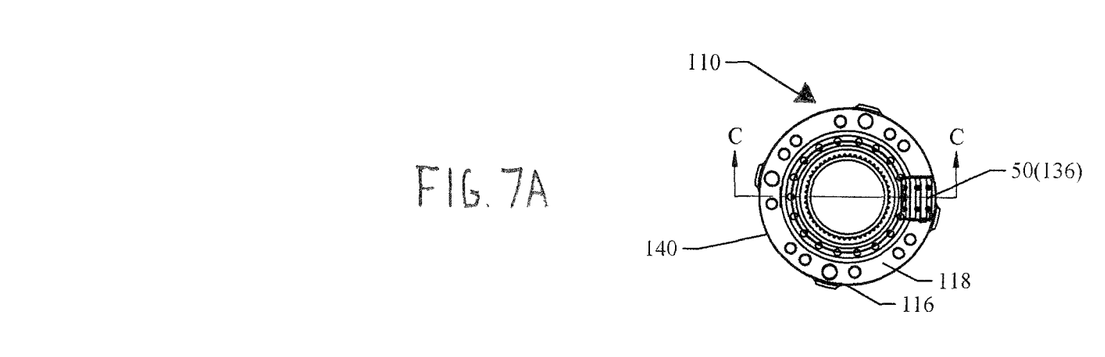
FIG. 7A is another top plan view of the metal component of FIG. 5.
Figure 7B:
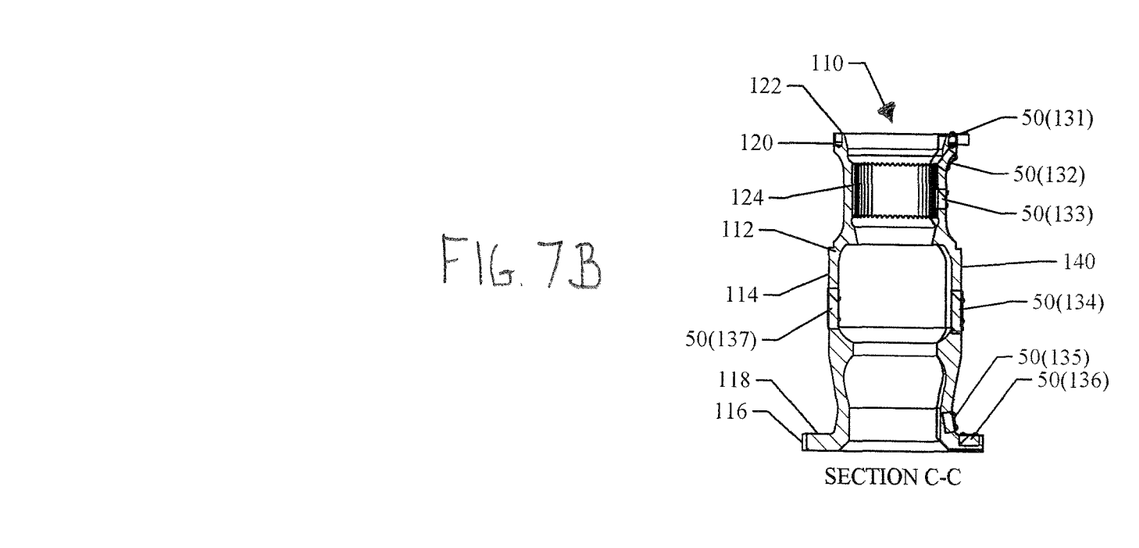
FIG. 7B is a cross-section of the metal component of FIG. 5 taken along line C-C of FIG. 7A.

A fourth step in the illustrated embodiment of the method for quantifying the metal surface treatment of component 100 comprises creating 2-D sketches using the solid model 110 and having the test strip mounting block assembly 50 positioned at locations 131-137. As shown in FIGS. 7A and 7B, portions 140 (shown outlined) of the solid model 110 are identified as elements of the solid model 110 upon which the test strip mounting block assembly 50 is mounted or otherwise supported.

Figure 8A:
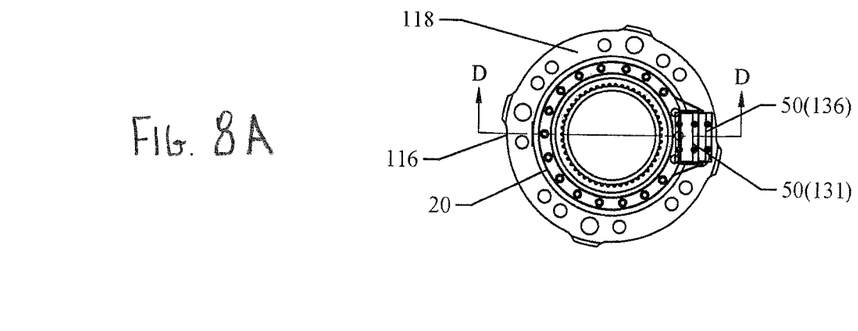
FIG. 8A is another top plan view of the metal component of FIG. 5.
Figure 8B:
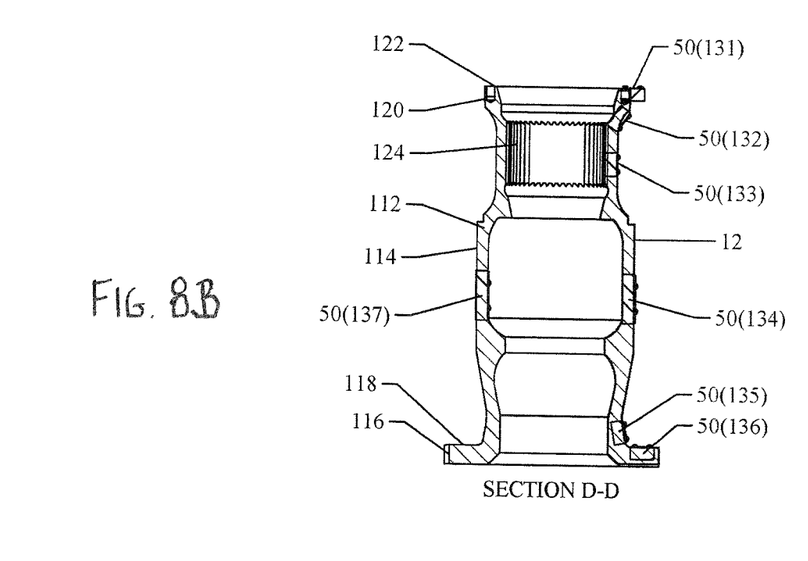
FIG. 8B is a cross-section of the metal component of FIG. 5 taken along line D-D of FIG. 8A.

In a fifth step in the illustrated embodiment of the method for quantifying the metal surface treatment of component 100, the 2-D sketches are modified, as shown in FIGS. 8A and 8B to provide scaled drawings (e.g., designs, blueprints, manufacturing plans, etc.) for fabricating components of a fixture that represent component 100 having a test strip mounting block assembly 50 positioned at locations 131-137. For example, top flange 120 is represented by a fixture component, top flange 20, wherein said top flange 20 is modified from top flange 120 to accommodate the mounting of a test strip mounting block assembly 50 thereon corresponding to location 131. Similarly, a portion of the body 112 is represented by a plurality of fixture components, uprights 12, wherein at least one of the uprights 12 is modified from the surface 114 of the body 112 to accommodate the mounting of a test strip mounting block assembly 50 thereon corresponding to locations 132-136.

As a result, scaled drawings for a fixture 10 (FIGS. 9-12B) representing the component 100, developed from the solid model 110, are prepared. As described herein, the fixture 10 simulates the component 100 during shot peening processing. The plurality of test strip mounting block assemblies 50 are supported by, or mounted on, the fixture 10 at the locations 132-137 where the intensity of the shot peening process is quantified, measured, and/or verified.

Figure 9:
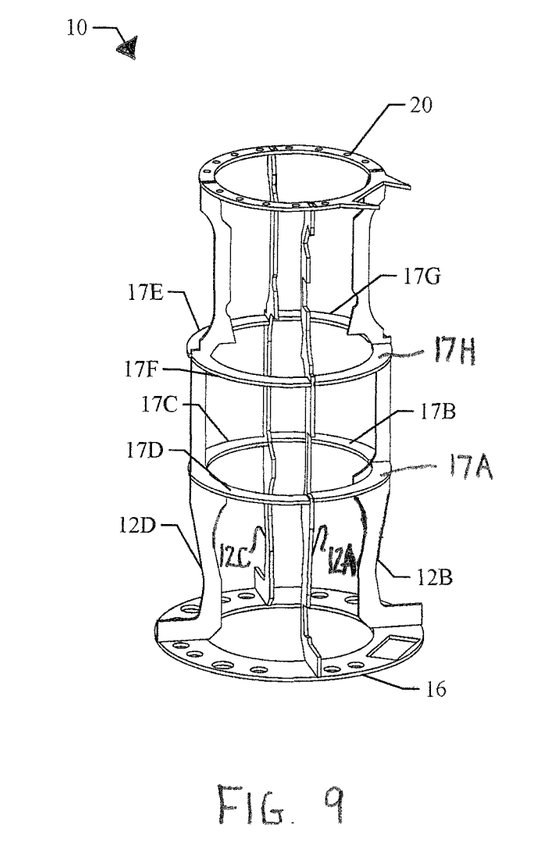
FIG. 9 is an isometric projection of a metal surface treatment fixture according to the present invention and corresponding to the metal component of FIG. 1.
Figure 10:
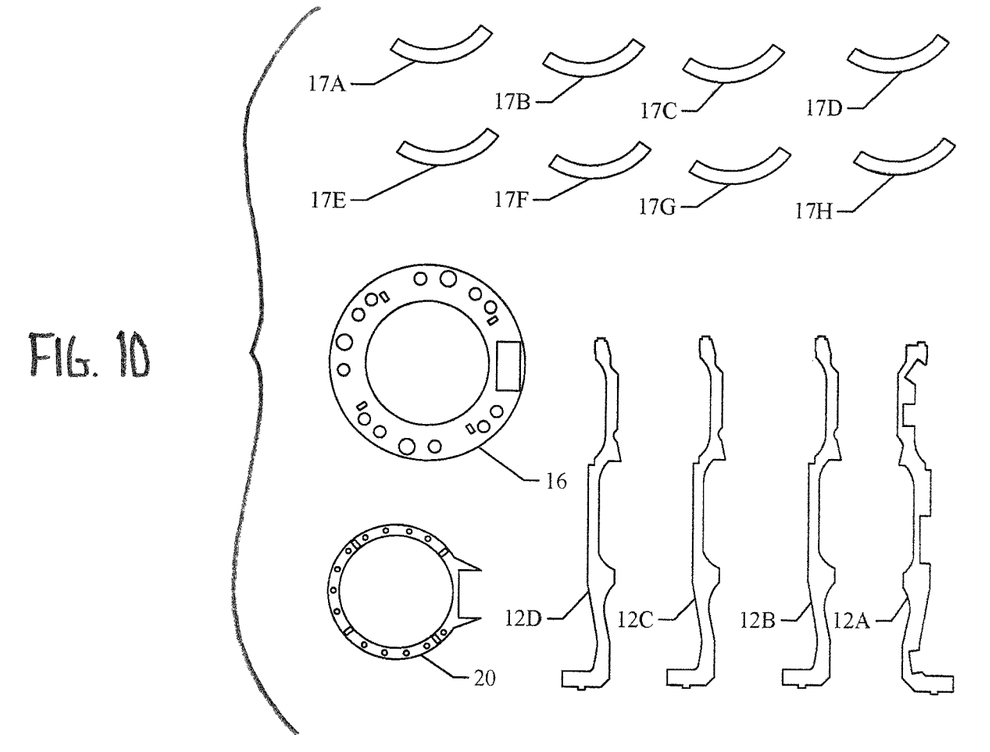
FIG. 10 provides schematic illustrations of a plurality of fixture components of the metal surface treatment fixture of FIG. 9.

In a sixth and final step in the illustrated embodiment of the method for quantifying the metal surface treatment of component 100, and as shown in FIGS. 9 and 10, the fixture 10 is assembled from fixture components fabricated in accordance with the scaled drawings. The fixture 10 comprises the top flange 20, four uprights 12A-12D, a bottom flange 16, and interconnecting elements 17A-17H. As can be seen, fixture components top flange 20, upright 12A, and bottom flange 16 have been modified to support the mounting of the test strip mounting block assemblies 50 thereon at the locations 132-136. Upright 12C and element 17C support the mounting of the test strip mounting block assembly 50 at location 137.

Figure 11:
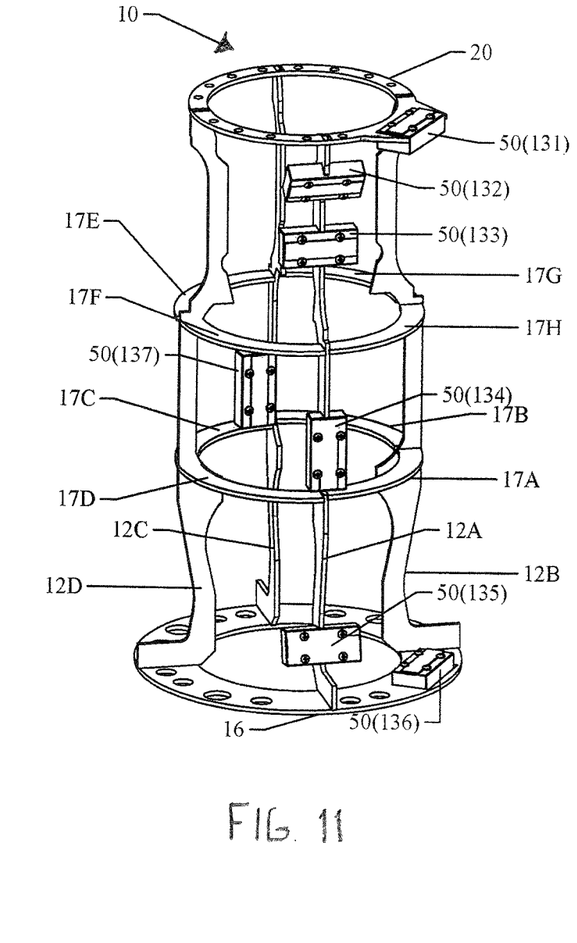
FIG. 11 is an isometric projection of the metal surface treatment fixture of FIG. 9 having a plurality of the Almen strip mounting blocks of FIG. 4 mounted thereon.
Figure 12A:
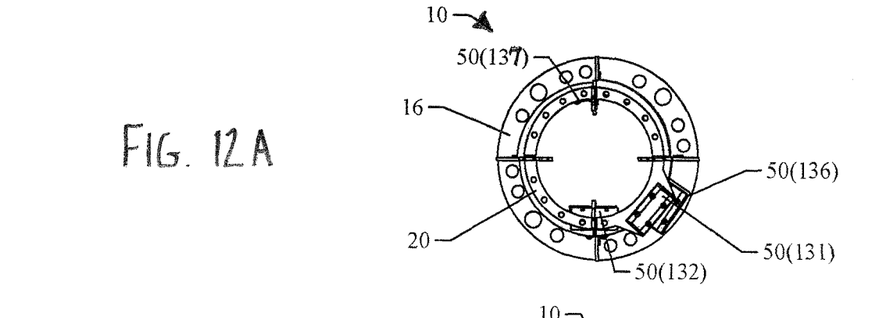
FIG. 12A is a top plan view of the metal surface treatment fixture of FIG. 11.
Figure 12B:
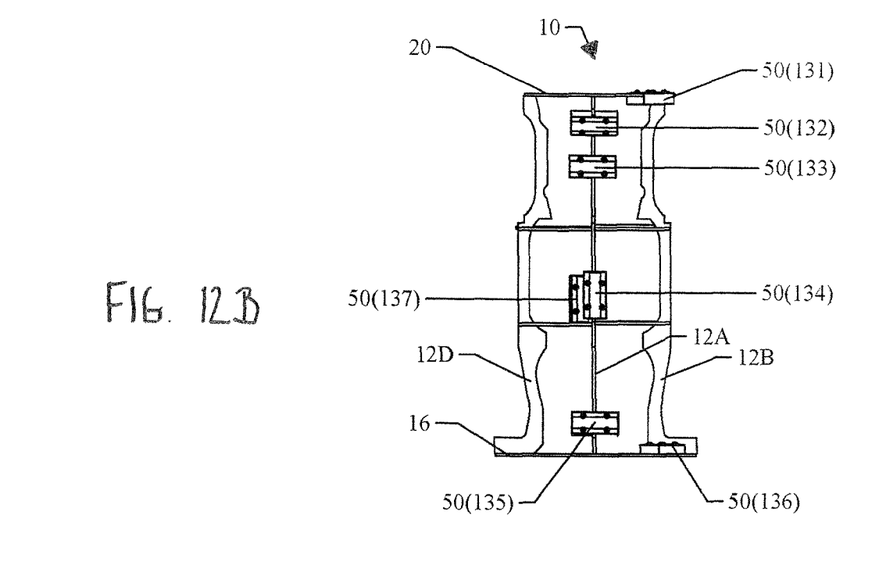
FIG. 12B is a side view of the metal surface treatment fixture of FIG. 11.

The fixture 10, having the test strip mounting block assemblies 50 mounted thereon at the locations 132-137, as shown in FIGS. 11, 12A and 12B, is then subjected to a shot peening process stream under substantially the same conditions to which the metal component 100 is subjected. Subsequently, the test strips 60 are removed from the blocks 52 for inspection and analysis; for example, the arc height and uniform coverage of the test strip 60 are examined and a set of results is obtained. A saturation curve is generated wherein the inspection, analysis, and/or examination results of the test strips 60 peened under the shot peening process conditions and for varying amounts of time are plotted. The saturation curve is plotted as a function of the "Arc Height" of at least one test strip 60 (as plotted along the vertical axis) measured at designated points in time or "Time in Minutes" (as plotted along the horizontal axis).

TABLE 1

ALMEN TEST STRIP READINGS

| Time (Minutes) | 0 | 2 | 4 | T-1 6 | T-2 12 | % Increase | Intensity: |
|---|---|---|---|---|---|---|---|
| TS-1 | 0 | 0.0050 | 0.0072 | 0.0080 | 0.0088 | 10.0% | 6-10 Å |

Note:
T-1 represents the saturation point; and T-2 represents the saturation point doubled.

For example, a set of results as shown in Table 1 was obtained from the examination of a test strip 60 having been subjected to a shot peening process stream under substantially the same conditions to which the metal component 100 will be subjected. Measurements of the arc height of an Almen test strip were obtained at least at one-minute intervals. As described above, saturation is reached when doubling the peening time has a 10% effect on the deflection of the test strip 60.

Figure 13:
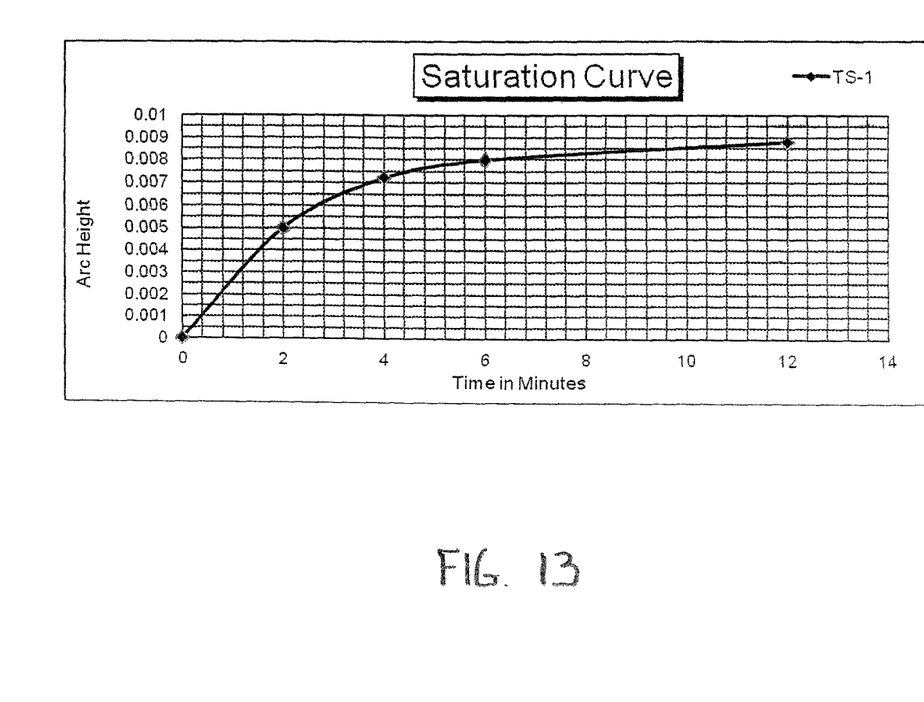
FIG. 13 is a graphical representation of a saturation curve generated by a set of results obtained from the examination of a test strip having been subjected to a shot peening process.

The set of results obtained and presented in Table 1 indicate that the peening time between the six-minute mark, T-1, and the twelve-minute mark, T2, respectively 0.0080 inch and 0.0088 inch, provides a 10% effect on deflection. Accordingly, the intensity of the shot peening process is about 6-10 Å ("Å" represents a unit of measurement known as an "angstrom" equal to $1 \times 10^{-10}$ meter.) The corresponding saturation curve presented in FIG. 13 graphically depicts the set of results presented in Table 1 as line TS-1, plotted as a function of the Arc Height versus elapsed Time in Minutes. The 10% effect on deflection is represented by the line TS-1 between the data point of 0.0080 inch plotted at the six-minute mark and the data point of 0.0088 inch plotted at the twelve-minute mark.

The shot peening process is adjusted or fine-tuned as a result of such inspection and analysis. Replacement test strips 60 are installed in the blocks 52 such that the fixture 10, having the test strip mounting block assemblies 50 mounted thereon at the locations 132-137, is subjected to the adjusted shot peening process. The shot peening process is finely tuned until the set of results obtained is within an acceptable limit or range sufficient to impart the metallurgical capabilities and structural properties specified for the component 100; for example, the peening intensity and coverage may be fine-tuned. Once the appropriate shot peening process has been established, the component 100 is subjected to the shot peening process and subsequently a set of metallurgical capabilities and structural properties are inspected, analyzed, tested and/or examined, particularly at the identified surface locations of the component 100 where such metallurgical capabilities and structural properties are specified by design.

An apparatus and/or method for evaluating the surface of a metal component after the metal component has been subjected to a surface treatment process in accordance with the present invention provides an efficient and economical solution for establishing the operating parameters of the surface treatment process necessary to impart the specified metallurgical capabilities and structural properties for a metal component without subjecting such metal component to repetitive processing before such operating parameters have been established. Accordingly, the number of metal components that must be inspected and analyzed, often by destructive means, is substantially reduced. Moreover, a greater number of part surfaces, including surfaces having a complex geometry, can be simulated by a fixture according to the present invention wherein such surfaces otherwise only could be inspected and analyzed by destructive means.

The above-described and illustrated embodiment of the present invention comprises an apparatus and a method for designing and fabricating a fixture to simulate a metal component that will be subjected to a shot peening process. The fixture enables the identification of precise locations for mounting test strip mounting block assemblies thereon to quantify the intensity and coverage of the shot peening of the selected surface(s) of the simulated component. It will be obvious to one skilled in the art to modify this embodiment of the present invention in order to quantify the application of any of a variety of surface treatment processes in addition to shot peening such as, for example, plating, galvanizing, painting, coating, spraying, polishing, etching and chemical milling, linishing, etc. Accordingly, all such modifications are considered within the scope of the present invention.

Although this invention has been shown and described with respect to the detailed embodiments thereof, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A method for measuring a metal surface treatment of a metal component comprising:
    creating a solid model of the metal component;
    identifying at least one surface location on the metal component at which a set of structural properties is specified by design;
    identifying a simulated location on the solid model corresponding to the at least one identified surface location on the metal component;
    preparing a simulation fixture plan for fabricating a simulation fixture having an element for supporting a test strip holder thereon at the identified simulated location;
    fabricating the simulation fixture;
    positioning at least one test strip holder at the identified simulated location on the simulation fixture;
    positioning a test strip in the test strip holder; and
    subjecting the simulation fixture to the metal surface treatment wherein the simulation fixture has the test strip holder positioned thereon and the test strip holder has the test strip positioned thereon.

2. The method for measuring a metal surface treatment of a metal component of claim 1 further comprising:
    identifying a plurality of surface locations on the metal component at which a set of structural properties is specified by design;
    identifying a plurality of simulated locations on the solid model corresponding to each of the plurality of identified surface locations on the metal component;
    preparing a simulation fixture plan for fabricating a simulation fixture having a plurality of elements for supporting a plurality of test strip holders thereon, one of the plurality of test strip holder at each of the plurality of identified simulated locations;

positioning one of the plurality of test strip holders at each of the plurality of identified simulated locations on the simulation fixture;

positioning a test strip in each of the plurality of test strip holders; and subjecting the simulation fixture to the metal surface treatment wherein the simulation fixture has the plurality of test strip holders positioned thereon and each of the plurality of test strip holders has the test strip positioned thereon.

3. The method for measuring a metal surface treatment of a metal component of claim 1 wherein the test strip is an Almen strip.

4. The method for measuring a metal surface treatment of a metal component of claim 1 wherein the metal surface treatment is a shot peening process.

5. The method for measuring a metal surface treatment of a metal component of claim 4 further comprising, subsequent to subjecting the simulation fixture to the metal surface treatment:

removing at least one of the test strips from the respective test strip holder positioned on the simulation fixture; and examining the test strip for at least one of shot peening intensity, coverage, and deflection, obtaining a set of results, and analyzing the set of results.

6. The method for measuring a metal surface treatment of a metal component of claim 5 wherein analyzing the set of results comprises generating a saturation curve.

7. The method for measuring a metal surface treatment of a metal component of claim 5 further comprising fine-tuning the shot peening process based upon the analysis of the set of results of the examination of the test strip.

8. The method for measuring a metal surface treatment of a metal component of claim 7 further comprising:

positioning a replacement test strip in each of the respective test strip holders positioned on the simulation fixture from which the test strip was removed; and subjecting the simulation fixture to the fine-tuned shot peening process wherein the simulation fixture has the test strip holders positioned thereon and the test strip holders have the test strip positioned thereon.

9. The method for measuring a metal surface treatment of a metal component of claim 8 wherein, subsequent to subjecting the simulation fixture to the fine-tuned shot peening process, the steps of removing at least one of the test strips from the respective test strip holder positioned on the simulation fixture, examining the test strip, obtaining a set of results, analyzing the set of results, and fine-tuning the shot peening process is repeated until the set of results is within an acceptable range.

10. The method for measuring a metal surface treatment of a metal component of claim 9 further comprising subjecting the metal component to the fine-tuned shot peening process.

11. The method for measuring a metal surface treatment of a metal component of claim 10 further comprising testing at least one of the identified surface locations on the metal component for the set of structural properties specified by design.

12. A method for establishing the operating parameters of a shot peening process of a metal component comprising:

creating a solid model of the metal component;

identifying at least one surface location on the metal component at which a set of structural properties will be measured;

identifying a simulated location on the solid model corresponding to each identified surface location on the metal component;

preparing a simulation fixture plan for fabricating a simulation fixture having an element for supporting a test strip holder thereon at each identified simulated location;

fabricating the simulation fixture;

positioning each test strip holder at each identified simulated location on the simulation fixture;

positioning a test strip in each test strip holder;

subjecting the simulation fixture to the shot peening process wherein the simulation fixture has the test strip holders positioned thereon and the test strip holders have the test strip positioned thereon;

removing at least one of the test strips from the respective test strip holder positioned on the simulation fixture;

examining the test strip for arc height and uniform coverage, obtaining a set of results, and analyzing the set of results;

fine-tuning the shot peening process based upon the analysis of the set of results of the examination of the test strip;

positioning a replacement test strip in each of the respective test strip holders positioned on the simulation fixture from which the test strip was removed; and subjecting the simulation fixture to the fine-tuned shot peening process wherein the simulation fixture has the test strip holders positioned thereon and the test strip holders have the test strip positioned thereon.

13. The method for establishing the operating parameters of a shot peening process of claim 12 wherein analyzing the set of results comprises generating a saturation curve.

14. The method for establishing the operating parameters of a shot peening process of claim 12 wherein the test strip is an Almen strip.

15. The method for establishing the operating parameters of a shot peening process of claim 12 wherein, subsequent to subjecting the simulation fixture to the fine-tuned shot peening process, the steps of removing at least one of the test strips from the respective test strip holder positioned on the simulation fixture, examining the test strip, obtaining a set of results, analyzing the set of results, and fine-tuning the shot peening process is repeated until the set of results is within an acceptable range.

16. The method for establishing the operating parameters of a shot peening process of claim 12 further comprising subjecting the metal component to the fine-tuned shot peening process.

17. The method for establishing the operating parameters of a shot peening process of claim 16 further comprising testing at least one of the identified surface locations on the metal component for a set of structural properties specified by design.

18. A method for shot peening a metal component comprising:

creating a solid model of the metal component;

identifying at least one surface location on the metal component at which a set of structural properties will be measured;

identifying a simulated location on the solid model corresponding to each identified surface location on the metal component;

preparing a simulation fixture plan for fabricating a simulation fixture having an element for supporting a test strip holder thereon at each identified simulated location;

fabricating the simulation fixture;

positioning each test strip holder at each identified simulated location on the simulation fixture;
positioning a test strip in each test strip holder;
subjecting the simulation fixture to the shot peening process wherein the simulation fixture has the test strip holders positioned thereon and the test strip holders have the test strip positioned thereon;
removing at least one of the test strips from the respective test strip holder positioned on the simulation fixture;
examining the test strip for at least one of shot peening intensity, coverage, and deflection, obtaining a set of results, and analyzing the set of results;
fine-tuning the shot peening process based upon the analysis of the set of results of the examination of the test strip;
positioning a replacement test strip in each of the respective test strip holders positioned on the simulation fixture from which the test strip was removed;
subjecting the simulation fixture to the fine-tuned shot peening process wherein the simulation fixture has the test strip holders positioned thereon and the test strip holders have the test strip positioned thereon;
repeating the steps of removing at least one of the test strips from the respective test strip holder positioned on the simulation fixture, examining the test strip, obtaining a set of results, analyzing the set of results, and fine-tuning the shot peening process until the set of results is within an acceptable range;
subjecting the metal component to the fine-tuned shot peening process; and
testing at least one of the identified surface locations on the metal component for the set of structural properties specified by design.

19. The method for shot peening a metal component of claim 18 wherein analyzing the set of results comprises generating a saturation curve.

20. The method for shot peening a metal component of claim 18 wherein the test strip is an Almen strip.

* * * * *